(12) United States Patent
Browder et al.

(10) Patent No.: US 12,645,345 B2
(45) Date of Patent: *Jun. 2, 2026

(54) METHOD AND SYSTEM FOR GENERATING A USER-SENSITIVE USER INTERFACE

(71) Applicant: Signet Health Corporation, North Richland Hills, TX (US)

(72) Inventors: Blake Browder, Dallas, TX (US); Joy Figarsky, Little Rock, AR (US)

(73) Assignee: Signet Health Corporation, North Richland Hills, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/193,119

(22) Filed: Apr. 29, 2025

(65) Prior Publication Data

US 2026/0147445 A1     May 28, 2026

Related U.S. Application Data

(63) Continuation of application No. 18/957,744, filed on Nov. 23, 2024, now Pat. No. 12,314,536.

(51) Int. Cl.
*G06F 3/0482* (2013.01)
*G06Q 50/26* (2012.01)
*G16H 40/20* (2018.01)

(52) U.S. Cl.
CPC ......... *G06F 3/0482* (2013.01); *G06Q 50/265* (2013.01); *G16H 40/20* (2018.01)

(58) Field of Classification Search
CPC .......................... G06F 3/048–05; G16H 40/20
See application file for complete search history.

(56) References Cited

U.S. PATENT DOCUMENTS 10,376,441 B2 * 8/2019 Oppenheimer ........ G16H 40/60
10,972,479 B2 * 4/2021 Clark .................... H04L 9/3239
(Continued)

FOREIGN PATENT DOCUMENTS

CN     113988577 A     1/2022
JP     2016110375 A    6/2016

OTHER PUBLICATIONS

Brian Tilow; Using Technology to Maintain Behavioral Health Safety Rounding and Nursing Workflows; Cleveland Clinic Nursing Informatics and Emerging Clinical Solutions Center Oct. 2017.

*Primary Examiner* — Daniel Rodriguez
(74) *Attorney, Agent, or Firm* — Caldwell LLC

(57) ABSTRACT

A system for generating a user-sensitive user interface, wherein the system includes a display device; at least a computing device, wherein the computing device comprises: a memory; and at least a processor connected to the memory, wherein the memory contains instructions configuring the at least a processor to: generate an execution operation as a function of a task module; display the execution operations in a user interface; receive, through the user interface, user response data corresponding to one or more of the execution operations; determine, as a function of the user response data, an assigned status corresponding the one or more execution operations using a machine-learning model; generate a second execution operation and an assigned node as a function of the assigned status; generate an updated user interface as a function of the second execution operation and the assigned status; and transmit the updated user interface to the assigned node.

16 Claims, 10 Drawing Sheets

(56) References Cited

U.S. PATENT DOCUMENTS

| | | | |
|---|---|---|---|
| 11,106,331 B1 * | 8/2021 | Porter | .................... G06Q 10/06 |
| 11,531,940 B2 * | 12/2022 | Gupta | ............ G06Q 10/063114 |
| 11,841,109 B2 | 12/2023 | Gold et al. | |
| 12,046,359 B2 | 7/2024 | Durlach et al. | |
| 2015/0154528 A1 * | 6/2015 | Kharraz Tavakol | ......................... |
| | | | G06Q 10/063114 |
| | | | 705/2 |
| 2019/0213509 A1 * | 7/2019 | Burleson | ................ G06N 20/00 |
| 2023/0229986 A1 * | 7/2023 | Cami | ................... G06Q 10/103 |
| | | | 705/7.15 |
| 2023/0334389 A1 | 10/2023 | Dalley, Jr. et al. | |

\* cited by examiner

200b

208

216a

216b

216j

Daily View

216k

December 7, 2024

Inspections

Ratings

216m

Cleaning Rounds

Access Controls

Room Specific

216l

216i

Room Cleaning 09-18-2024
Room Cleaning 09-27-2024
Room Cleaning 09-31-2024
Room Cleaning 10-18-2024
Room Cleaning 10-23-2024
Room Cleaning 11-08-2024

216c 216d      216e      216f

216g

200d

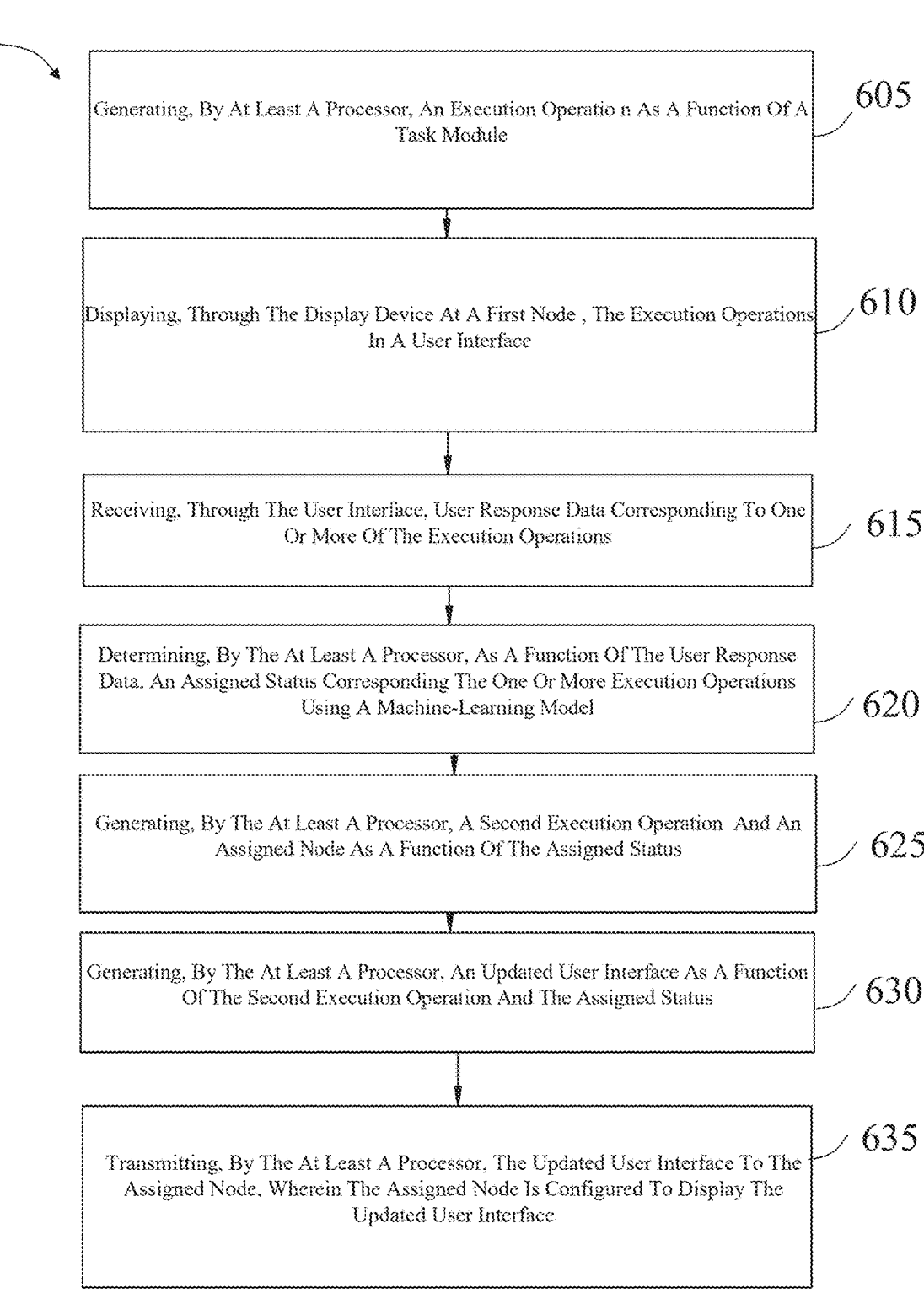

600

Generating, By At Least A Processor, An Execution Operatio n As A Function Of A
Task Module                                                                                605

Displaying, Through The Display Device At A First Node , The Execution Operations
In A User Interface                                                                        610

Receiving, Through The User Interface, User Response Data Corresponding To One
Or More Of The Execution Operations                                                       615

Determining, By The At Least A Processor, As A Function Of The User Response
Data, An Assigned Status Corresponding The One Or More Execution Operations
Using A Machine-Learning Model                                                            620

Generating, By The At Least A Processor, A Second Execution Operation  And An
Assigned Node As A Function Of The Assigned Status                                        625

Generating, By The At Least A Processor, An Updated User Interface As A Function
Of The Second Execution Operation And The Assigned Status                                 630

Transmitting, By The At Least A Processor, The Updated User Interface To The
Assigned Node, Wherein The Assigned Node Is Configured To Display The
Updated User Interface                                                                    635

FIG. 6

METHOD AND SYSTEM FOR GENERATING A USER-SENSITIVE USER INTERFACE

CROSS-REFERENCE TO RELATED APPLICATIONS

This application is a continuation of Non-provisional application Ser. No. 18/957,744, filed on Nov. 23, 2024, and entitled "METHOD AND SYSTEM FOR GENERATING A USER-SENSITIVE USER INTERFACE," the entirety of which is incorporated herein by reference.

FIELD OF THE INVENTION

The present invention generally relates to the field of user interfaces. In particular, the present invention is directed to a method and system for generating a user-sensitive user interface.

BACKGROUND

Modern graphical user interfaces (GUIs) often lack the adaptability and intelligence needed to handle dynamic, real-time task management in environments that require constant monitoring and updates. Current systems typically rely on static checklists and manual data input, limiting their ability to provide real-time feedback or generate automated follow-up actions based on user inputs.

SUMMARY OF THE DISCLOSURE

In some aspects, the techniques described herein relate to a system for generating a user-sensitive user interface, wherein the system includes: at least a computing device, wherein the computing device includes: a memory; and at least a processor communicatively connected to the memory, wherein the memory contains instructions configuring the at least a processor to: receive user response data corresponding to one or more of execution operations; determine, as a function of the user response data, an assigned status corresponding to the one or more execution operations using a machine-learning model; generate a second execution operation as a function of the assigned status; generate an updated user interface as a function of the second execution operation and the assigned status; and transmit the updated user interface to an assigned node.

In some aspects, the techniques described herein relate to a method for generating a user-sensitive user interface, wherein the method includes: receiving, using at least a processor, user response data corresponding to one or more of execution operations; determining, using the at least a processor and as a function of the user response data, an assigned status corresponding to the one or more execution operations using a machine-learning model; generating, using the at least a processor, a second execution operation as a function of the assigned status; generating, using the at least a processor, an updated user interface as a function of the second execution operation and the assigned status; and transmitting, using the at least a processor, the updated user interface to an assigned node.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention.

However, it should be understood that the present invention is not limited to the precise arrangements and instrumentalities shown in the drawings, wherein:

FIG. 6 is a block diagram of an exemplary method for generating a user-sensitive user interface;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a user-sensitive user interface. In an embodiment, a system for generating a user-sensitive user interface, wherein the system comprises: a display device, wherein the display device is configured to display a graphical user interface; at least a computing device, wherein the computing device comprises: a memory; and at least a processor communicatively connected to the memory, wherein the memory contains instructions configuring the at least a processor to: generate an execution operation as a function of a task module; display, through the display device at a first node, the execution operations in a user interface; receive, through the user interface, user response data corresponding to one or more of the execution operations; determine, as a function of the user response data, an assigned status corresponding the one or more execution operations using a machine-learning model; generate a second execution operation and an assigned node as a function of the assigned status; generate an updated user interface as a function of the second execution operation and the assigned status; and transmit the updated user interface to the assigned node, wherein the assigned node is configured to display the updated user interface.

Aspects of the present disclosure allow for a user-sensitive user interface. Exemplary embodiments illustrating aspects of the present disclosure are described below in the context of several specific examples.

Figure 1:
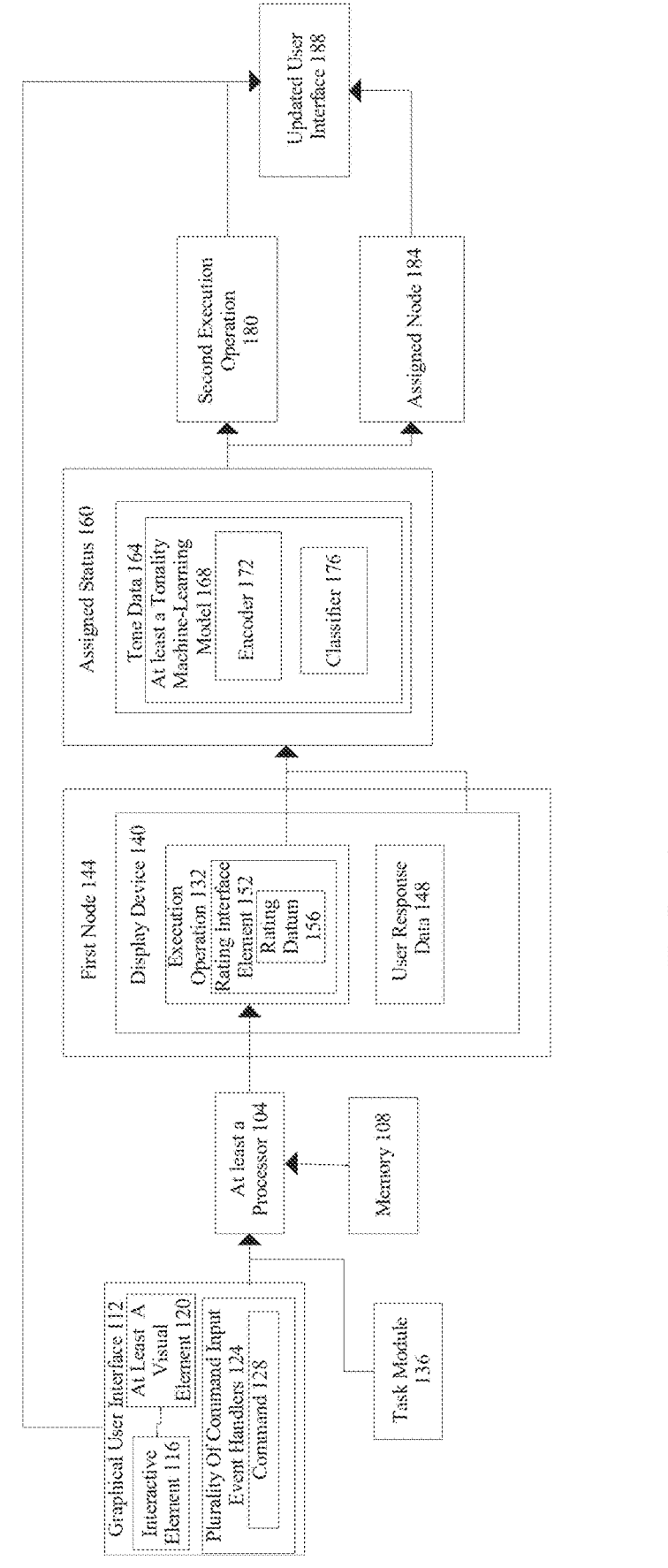
FIG. 1 is a flow diagram illustrating a system for generating a user-sensitive user interface.

Referring now to FIG. 1, an exemplary embodiment of a system 100 for generating a user-sensitive user interface is illustrated. System 100 may include a processor 104 communicatively connected to a memory 108. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor 104. In one or more embodiments, data is transferred from secondary to primary memory wherein processor 104 may access the information from primary memory.

Still referring to FIG. 1, system 100 may include a database. The database may include a remote database. The database may be implemented, without limitation, as a relational database, a key-value retrieval database such as a NOSQL database, or any other format or structure for use as database that a person skilled in the art would recognize as suitable upon review of the entirety of this disclosure. The database may alternatively or additionally be implemented using a distributed data storage protocol and/or data structure, such as a distributed hash table or the like. The database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments, the computing device may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by the system. In one or more embodiments, computing device may transmit processes to server wherein computing device may conserve power or energy.

Further referring to FIG. 1, system 100 may include any "computing device" as described in this disclosure, including without limitation a microcontroller, microprocessor, digital signal processor (DSP) and/or system on a chip (SoC) as described in this disclosure. System 100 may include, be included in, and/or communicate with a mobile device such as a mobile telephone or smartphone. System 100 may include a single computing device operating independently, or may include two or more computing devices operating in concert, in parallel, sequentially or the like; two or more computing devices may be included together in a single computing device or in two or more computing devices. System 100 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. System 100 may include one or more computing devices dedicated to data storage, security, distribution of traffic for load balancing, and the like. System 100 may distribute one or more computing tasks as described below across a plurality of computing devices of computing device, which may operate in parallel, in series, redundantly, or in any other manner used for distribution of tasks or memory between computing devices. System 100 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, processor 104 generates a graphical user interface 112 comprising at least an interactive element 116 associated with at least a visual element 120 configured to receive user response data 148. A "graphical user interface," as used herein, is a graphical form of user interface that allows users to interact with electronic devices. In some embodiments, GUI 112 may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages, and the like may be represented using a small picture in a graphical user interface. For example, links to decentralized platforms as described in this disclosure may be incorporated using icons. Using an icon may be a fast way to open documents, run programs etc. because clicking on them yields instant access.

As used in this disclosure, an "interactive element" is a component within a system, interface, or device that allows a user to engage with and influence the system's behavior or output through actions. In a non-limiting example, the actions may include clicking, touching, or inputting data. Without limitation, the interactive element 116 may respond dynamically to the user response data 148, enabling real-time feedback or control over system functions. For example, without limitation the interactive element 116 may include buttons, sliders, input fields, or menus in software interfaces, as well as physical controls like switches or touchscreens in hardware devices. Each interactive element of a plurality of interactive elements may comprise an event handler configured to detect an interaction and generate response data as a function of the interaction.

As used in this disclosure, a "visual element" is a component or feature within a system, display, or interface that conveys information through visual means. In a non-limiting example, the visual element 120 may include text, images, icons, shapes, colors, and/or other graphical components designed to be perceived by the user. In a non-limiting example, the visual element 120 may aid in communication, navigation, and/or interaction with the system. Without limitation, the visual element 120 may be used to enhance user experience, guide behavior, and/or represent data visually in an intuitive or informative way. A visual element 120 may include any data transmitted to display device, client device, and/or graphical user interface 112. In some embodiments, visual element 120 may be interacted with. For example, visual element 120 may include an interface, such as a button or menu. In some embodiments, visual element 120 may be interacted with using a user device such as a smartphone, tablet, smartwatch, or computer.

Still referring to FIG. 1, processor 104 displays, using the graphical user interface 112, a plurality of command input event handlers 124 wherein a command 128 in the plurality of command input event handlers 124 corresponds to the at least a visual element 120. As used in this disclosure, a "command input event handler" is a is a structured list of tasks, instructions, and/or operations that are organized in a specific sequence. In a non-limiting example, the plurality of command input event handlers 124 may include at least a command 128. As used in this disclosure, a "command" is an instruction or directive given to a person, system, device, and/or process to perform a specific action or task. Without limitation, the command 128 may initiate an operation, alter system behavior, or trigger a response, and may be issued manually by a user or automatically by a program or system. In a non-limiting example, the command 128 may control hardware functions, execute software routines, or interact with external systems, and may be part of a sequence within the plurality of command input event handlers 124. In a non-limiting example, the command 128 may be awaiting execution or confirmation from a user. In a non-limiting example, the plurality of command input event handlers 124 may function as a checklist where each command 128 or task may be processed, executed, or marked as completed by the user or system.

With continued reference to FIG. 1, processor 104 may be configured to generate execution operations 132 as a function of a task module 136. As used herein, a "task module" refers to an environmental rounding action item. Environmental rounding may refer to actions used in healthcare, facilities management, and other industries to regularly inspect and assess the physical environment for safety, cleanliness, functionality, and other factors that could impact operations or the well-being of individuals. Non-limiting examples of task module 136 may include identifying issues such as clutter, equipment malfunctions, hazards, cleanliness concerns, and the like. As used herein, "execution operation" refers to the process that implements corrective or preventive actions on the issues identified during environmental rounds. Execution operations 132 may refer to a process that is generated as a function of task module 136 that has been identified. In a non-limiting embodiment, execution operations 132 may include identifying specific action items during the environmental rounding procedures, prioritizing tasks, cleaning, organizing, and the like. Each execution operation of the execution operations 132 may be linked to a plurality of interactive elements. Generating the execution operations 132 may include a rating interface element 152. As used herein, a "rating interface element" is a GUI component that allows for feedback by assigning a rating, in the form of a score, based on their experience or opinion. The rating interface element 152 may include a rating datum 156. A rating datum 156 may indicate satisfaction or preferences regarding a product, service, content, task module completion, and the like. In a non-limiting embodiment, rating surface elements may include a star rating, allowing for a selecting of a number of stars (possibly out of 5) to rate effectiveness of completion of task module 136 or execution operations 132. In another non-limiting embodiment, rating surface element may include a thumbs up/thumbs down icon to indicate approval or disapproval regarding the task module 136 or execution operations 132. In another non-limiting embodiment, rating surface element may include a numeric rating, allowing for a rating on a numerical scale (e.g., 1 to 10), allowing for a more granular feedback system. In another non-limiting embodiment, rating surface element may include a slider or dial to set a specific rating within a range, offering a dynamic and interactive way to rate the task module 136 or execution operations 132. In an embodiment, the GUI 112 may be updated as a function of rating interface element 152. This may indicate that the appearance, behavior, or content of the interface dynamically changes based on the feedback or input provided through the rating element. For example, after a rating datum is received, the GUI may provide instant visual feedback, such as highlighting selected stars or displaying a confirmation message. Real-time data updates, like recalculating the average rating, may also occur, while personalized recommendations can appear based on the input. If a low rating is given, the GUI might prompt for further feedback or offer support, whereas high ratings could unlock additional features or exclusive content.

Still referring to FIG. 1, system 100 may be configured to display, through the display device 140 at a first node 144, the execution operations in the GUI. As used in this disclosure, a "display device" refers to an electronic device that visually presents information to the entity. In some cases, display device 140 may be configured to project or show visual content generated by computers, video devices, or other electronic mechanisms. In some cases, display device may include a liquid crystal display (LCD), a cathode ray tube (CRT), a plasma display, a light emitting diode (LED) display, and any combinations thereof. In a non-limiting example, one or more display devices may vary in size, resolution, technology, and functionality. Display device 140 may be able to show any data elements and/or visual elements 120 as listed above in various formats such as, textural, graphical, video among others, in either monochrome or color. Display device may include, but is not limited to, a smartphone, tablet, laptop, monitor, tablet, and the like. Display device may include a separate device that includes a transparent screen configured to display computer generated images and/or information. In some cases, display device may be configured to present a graphical user interface to a user, wherein a user may interact with a GUI 112. In some cases, a user may view a GUI 112 through display.

Additionally, or alternatively, processor 104 may be connected to display device. As used herein "a first node" is a point in a computer network where data can be stored, created, sent, or received. The first node refers to the point where the execution operation is created. The first node 144 may initiate the execution operation. The first node 144 may initiate the execution operations 132. In an embodiment, first node 144 may refer to a first user.

Still referring to FIG. 1, system 100 may be configured to receive, through the GUI 112, user response data 148 corresponding to one or more of the execution operations 132. As used herein, "user response data" refers to information collected, such as feedback, rating, reviews or any other form of interaction that reflects an experience or interaction. User response data 148 may correspond to specific actions or procedures corresponding to one or more of the execution operations 132. User response data 148 may indicate that follow up action is required following completion of the one or more execution operations. User response data 148 may indicate that the one or more execution operations were not completed effectively. User response data 148 may be received using a chatbot interface configured to receive a textual response style detailing the completeness or effectiveness of an execution operation. User response data 148 may be received through a text-box interface displayed within the GUI. Examples of user response data 148 may include phrases such as, but not limited to, "poor quality," "needs to be cleaned again," "rude staff," "looks great," and the like. In another embodiment, user may flag maintenance issues, which may include actions that were not necessarily completely incorrectly, but may need further adjustments.

Still referring to FIG. 1, at least a processor 104 may determine, as a function of the user response data, an assigned status 160 corresponding to the one or more execution operations using a machine learning model. As used herein, an "assigned status" refers to a designation given to the one or more execution operations regarding completion or effectiveness of completion. Assigned status 160 may be determined as a function of the user response data, where determining the assignment data may include analyzing the user response data using at least a tonality machine-learning model 168 to determine tone data 164. As used herein, a least a "tonality machine-learning model" refers to a machine learning model that is trained to determine an effective tone of user response data. At least a tonality machine-learning model 168 may be trained using tonality training data. Tonality training data may include user response data as inputs and outputs a corresponding tone to the user response data. Tonality training data may include historical user response data, examples of user response data, feedback about user response data, feedback about corresponding tones of user response data, example corresponding tones of user response data, and the like as inputs into the at least a tonality machine-learning model. At least a tonality machine-learning model may be iteratively retrained using feedback regarding the effectiveness of outputs. The effectiveness of outputs of the at least a tonality machine-learning model 168 may be determined using a scoring system, a variance calculation, or system feedback regarding how closely the predicted corresponding tone of the user response data correctly aligns with the actual intended tone of the user response data. In an embodiment, the at least a tonality machine-learning model 168 may include an encoder 172 configured to generate a plurality of textual encodings as a function of the user response data 148 and a classifier configured to classify the plurality of textual encodings into a tone classification. As used herein, an "encoder" refers to a component within a machine-learning model that converts raw input data, such as text, into a set of structured numerical representations, known as encodings. The encodings may be configured to capture features of inputs, such as semantic meaning, linguistic patterns, and contextual relationships, which may allow the at least a tonality machine-learning model 168 to effectively interpret the underlying tone or sentiment of the user response data 148. In an embodiment, the encoder 172 may be trained using a self-supervised training process. A self-supervised training process is a machine learning approach where a model learns patterns, features, or representations within data without relying on manually labeled examples. Instead, the model generates its own labels or "pseudo-labels" from the raw data itself, often by predicting parts of the data from other parts. This process involves setting up tasks (or "pretext tasks") that allow the model to learn relationships within the data, using the data's inherent structure to guide learning. In an embodiment, the output of the encoder may be fed into a decoder which may be configured to estimate user response data. In another embodiment, the encoder is trained as a function of the estimated user response data that has been appended with a tone label. As used herein, a "tone label" is a label applied to a user response datum that is generated using the at least a tonality machine-learning model. In an embodiment, the classifier 176 may be configured to use the textual encodings to categorize the user response data into various tone classifications (e.g. positive, negative, neutral), which can enable system 100 to become more efficient at recognizing and responding to emotional or tonal subtleties in the user response data. The classifier 176 may be trained using classifier training data, which includes tonality training data comprising historical user responses and their associated tone classifications. The tonality machine-learning model refines its performance over time by iteratively retraining on feedback regarding the accuracy of its tone predictions. This feedback may be based on scoring systems, variance calculations, or system responses, which evaluate how well the predicted tone aligns with the intended user tone. Furthermore, historical input and output data may also serve as part of the classifier training data, enabling the system to learn from past interactions and improve its ability to classify future user responses accurately. The classifier 176, working in conjunction with the encoder and tonality machine-learning model, enables system 100 to adapt dynamically, ensuring that the graphical interface responds accurately and contextually to user input across varied interactions.

Still referring to FIG. 1, at least a processor 104 may be configured to generate a second execution operation 180 and an assigned node 184 as a function of the assigned status. As used herein, a "second execution operation" refers to a follow-up execution operation indicating additional tasks or action items. The assigned status designation given to the one or more execution operations 180 regarding completion or effectiveness of completion may be used to generate the second execution operations 132. For instance, if an execution operations 132, such as checking the cleanliness of a room, is flagged as "not compliant" or "follow-up required," the system 100 may automatically generate a second execution operations 132 to address the unresolved issue. Examples of second execution operations 180 may include tasks like rewashing sheets that were insufficiently cleaned, re-cleaning floors that didn't meet cleanliness standards, double-checking lighting to ensure it functions correctly, performing a secondary checklist verification to ensure all items were appropriately addressed, and the like. The assigned status given to the execution operation, which may reflect whether the task was completed or its level of effectiveness, serves as the trigger for generating the second execution operations 132. This process ensures that any outstanding issues are addressed through an additional round of tasks, thereby improving the overall quality and consistency of the operations. Furthermore, the second execution operation may be automatically assigned to the relevant personnel, ensuring prompt action and efficient workflow management. In an embodiment, at least a processor 104 may be configured to generate an assigned node 184 as a function of the assigned status 160. As used herein, "an assigned node" is a secondary point in a computer network where data can be stored, created, sent, or receive The assigned node 184 may serve as a control hub for managing the second execution operations, ensuring that they are appropriately executed based on the outcome of the execution operations 132. For instance, if the execution operation is marked as incomplete or requiring further action (e.g., "follow-up required"), the assigned node 184 may be generated to initiate the second execution operations 132, which may include tasks such as rewashing sheets, cleaning floors, double-checking lighting, or performing a secondary checklist verification. The assigned node 184 may operate by actively monitoring the assigned status and automatically triggering the necessary follow-up tasks, thereby ensuring that any unresolved issues from the first operation are addressed. The assigned node 184 may also be configured to interact with other system components to allocate resources, assign personnel, and track the progress of the second execution operations 132. By automating the initiation of secondary tasks through the assigned node, the system reduces manual oversight and improves operational efficiency, ensuring that all tasks, whether initial or follow-up, are executed with accuracy and timeliness. In an embodiment, generating the second execution operation 180 and the assigned node as a function of the assigned status may include classifying the second execution operation to an end user pool and selecting an end user from the end user pool wherein the end user has an associated with the assigned node. As used herein, end-user pool, refers to a collection of users grouped according to relevant qualifications, skills, or access levels. This classification ensures that the operation is directed toward a group of users with the expertise or authorization to handle the specific task effectively. The system may select an individual end-user from within this pool, matching the end-user's profile to the assigned node associated with the operation's requirements. The selected end-user may have relevant qualifications or permissions linked to the assigned node, ensuring the execution operation is handled by someone suited to its specific demands. If the initially assigned node declines the task—for instance, due to unavailability or task complexity—a new assigned node would be generated. The system may then reclassify and reassess available end-users within the pool, identifying a new candidate with the qualifications to handle the operation. This reassignment can ensure task continuity even when an end-user may be unable to accept the initial assignment. Additionally, workload balance may influence the selection of the assigned node. The processor may evaluate each node's current task load by querying other nodes for information on their active tasks, selecting an end-user from a node with the least number of pending tasks.

Continuing reference to FIG. 1, in an embodiment, the at least a processor 104 may be configured to display the second execution operation through the display device at the first node. The first node 144 refers to the initial point of interaction or the interface where the execution operations 132 was displayed and managed. By displaying the second execution operations 132 at the first node 144, the system ensures continuity and context for the user, allowing them to seamlessly transition from reviewing or managing the initial task to addressing the follow-up operation. For example, if the initial execution operation involved verifying the cleanliness of a room and was flagged as requiring follow-up (e.g., "follow-up required" or "not compliant"), the second execution operation, such as rewashing sheets or re-cleaning floors, may automatically appear on the same display device where the first node 144 managed the execution operations 132. This may allow the first node 144 to stay informed and take immediate action without navigating to a different part of the system or device. In an embodiment, the at least a processor 104 dynamically updates the display to reflect the status change and the initiation of the second execution operation, ensuring that all related tasks may be tracked and visible in real-time. In a non-limiting embodiment, the display of the second execution operation at the first node may ensure that users are promptly alerted to any additional tasks or actions required, allowing them to address outstanding issues without delay. This also may provide a consolidated task management view, where both initial and second execution operations can be monitored and tracked.

Continuing reference to FIG. 1, the at least a processor 104 may be configured to generate an updated user interface 188 as a function of the second execution operations 132 and the assigned status 160. The updated user interface could dynamically adjust based on the status of the execution operations 132 and any corresponding follow-up tasks associated with the second execution operations 132. By incorporating the assigned status, which may indicate the completion or effectiveness of the initial task, the processor may modify the user interface to reflect the new set of required actions indicated by second execution operations 132. For example, if an initial task, such as verifying room cleanliness, is flagged for follow-up (e.g., "follow-up required"), the system may generate a second execution operation, such as rewashing or re-cleaning, and display it within the updated interface. The assigned status from the initial task may be represented visually, ensuring the user is aware that additional actions could be required. This update may include modifications to visual elements such as task lists, icons, color codes, or priority indicators to highlight new tasks generated from the second execution operation. The updated user interface may also track the progress of the second execution operation in real-time, potentially providing users with visibility into ongoing tasks, deadlines, or workflow status. In some embodiments, the updated interface may include contextual prompts or alerts related to the second execution operation, ensuring that users are aware of any necessary actions without needing to manually locate additional information.

Still referring to FIG. 1, at least a processor 104 may be configured to transmit the updated user interface 188 to the assigned node 184, wherein the assigned node 184 is configured to display the updated graphical user interface 188. This transmission could occur once the processor has processed the second execution operations 132 and the assigned status 160, ensuring that the updated interface 188 is reflected at the appropriate location for node interaction. The updated user interface may provide a clear and organized view of tasks, such as the second execution operation, which may include various visual indicators, task lists, and real-time progress tracking. The assigned node could be situated at a specific workstation, mobile device, or another user access point, allowing the relevant node to interact with the system efficiently and monitor the ongoing operations. Additionally, the processor 104 may be configured to ensure that the updated user interface is dynamically transmitted to the assigned node in real-time or at specific intervals, depending on the system's requirements. This ensures that any changes made to the second execution operation 180 or assigned status 160 are immediately visible to the user. In some embodiments, the assigned status 160 may further enable user interaction with the updated interface, allowing the user to input feedback, mark tasks as completed, or trigger additional actions. This capability could ensure that the workflow remains adaptable and responsive, as the system dynamically adjusts based on user inputs received at the assigned node.

Figure 2A:
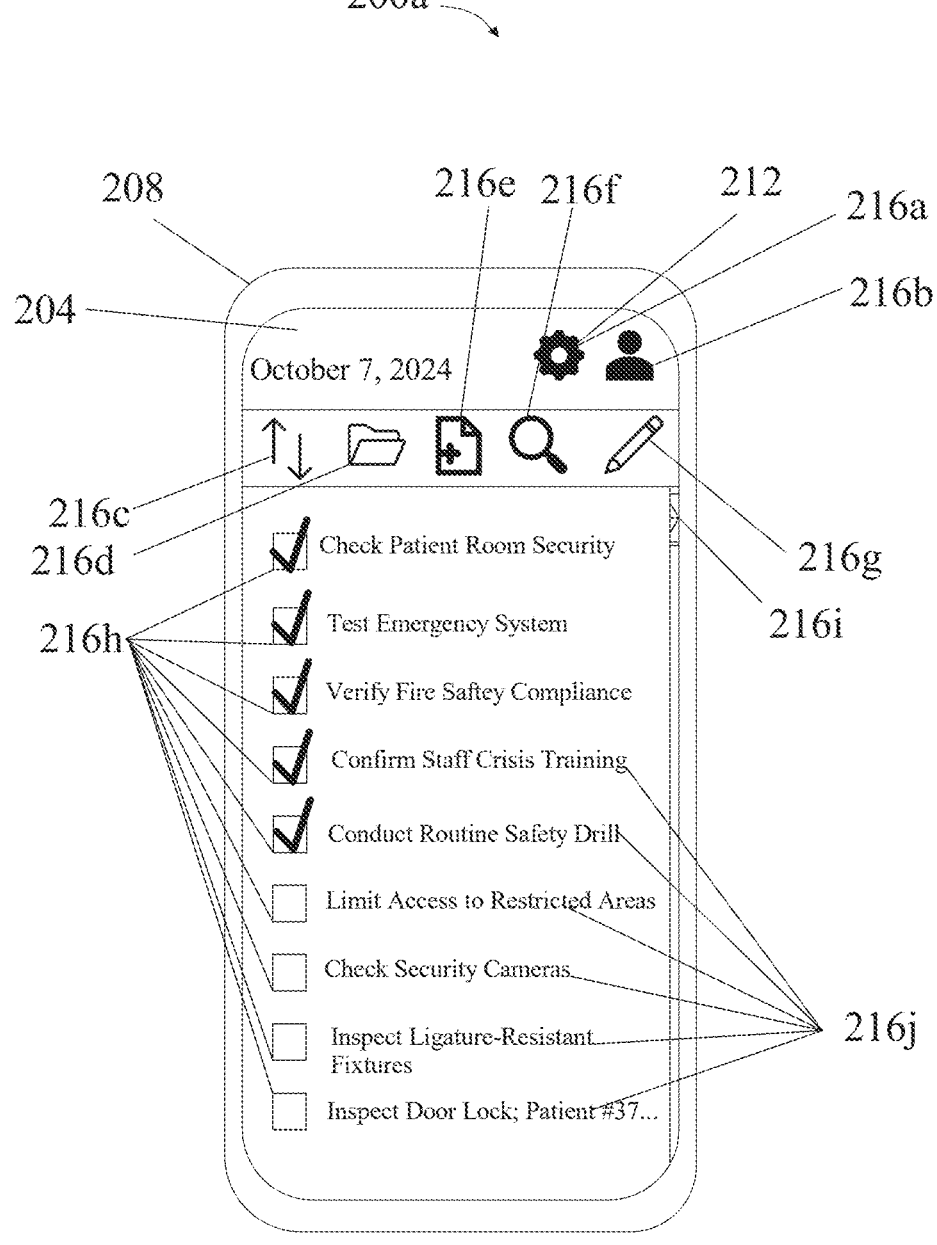
FIG. 2A is an exemplary illustration of a graphical user interface.

Referring now to FIG. 2A, an exemplary illustration 200*a* of a graphical user interface. In an embodiment, the graphical user interface 204 may be displayed using a downstream device 208. In an embodiment, the graphical user interface 204 may include at least a visual element 212. In an embodiment, the visual element 212 may include an interactive element 216. In an embodiment the interactive element 216 may allow a user to engage directly with the graphical user interface 204 through a variety of actions.

In an embodiment, the interactive element 216*a-m* may include a settings gear 216*a*, a profile icon 216*b*, a sorting icon 216*c*, a folder icon 216*d*, a new task icon 216*e*, a find icon 216*f*, an edit icon 216*g*, a check box icon 216*h*, a scroll bar icon 216*i*, text description 216*j*, and the like.

In an embodiment, the interactive element 216 may include a settings gear 216*a*. In an embodiment, the settings gear 216*a* may enable users to access the system or application settings where they may modify preferences and configurations. Without limitation, by clicking on the settings gear 216*a*, users may adjust features like notifications, display options, account details, and the like. In an embodiment, the settings gear 216*a* may represent control over personalizing the environment within the application. In an embodiment, the settings gear 216*a* may ensure that users can customize their experience to meet their specific needs.

In an embodiment, the interactive element 216 may include a profile icon 216*b*, which may allow users to access their personal profile settings. In an embodiment, the profile icon 216*b* may link to a page where users may view and edit their personal information, such as their name, contact details, or profile picture. In an embodiment, the profile icon 216*b* may make it simple for users to manage their account and view related data quickly. In an embodiment, the profile icon 216*b* may be placed in a convenient location, allowing easy access to account settings. In an embodiment, the profile icon 216*b* may help users maintain control over their profile, ensuring that their information stays up-to-date.

In an embodiment, the interactive element 216 may include a sorting icon 216*c*, which may allow users to organize data based on specific criteria. In an embodiment, the sorting icon 216*c* may be useful when dealing with large datasets or lists that need to be filtered or reordered. Without limitation, by clicking the sorting icon 216*c*, users may arrange items by various attributes such as date, name, priority, and the like. In an embodiment, the sorting icon 216*c* may simplify the process of locating specific information, making the interface more efficient to use. In an embodiment, the sorting icon 216*c* may ensure that users can easily customize how they view and interact with the content.

In an embodiment, the interactive element 216 may include a folder icon 216*d*, which may represent access to a file or document management system. Without limitation, by clicking on the folder icon 216*d* it may open a directory or list of stored files, allowing users to organize their content within the application. In an embodiment, the folder icon 216*d* may be essential for managing documents, media, or other file types efficiently. In an embodiment, the folder icon 216*d* may be associated with file storage and navigation, making it a familiar and intuitive tool for users. In an embodiment, the folder icon 216*d* may aid in keeping information organized and accessible within the system.

In an embodiment, the interactive element 216 may include a new task icon 216*e*, which may allow users to create or add a new item to their task list or project. In an embodiment, the new task icon 216*e* may provide a quick way for users to input new assignments or goals, streamlining task management. In an embodiment, the new task icon 216*e* once clicked, may open a form or prompt where users may specify details about the new task. In an embodiment, the new task icon 216*e* may help users stay organized by adding tasks efficiently as they arise. In an embodiment, the new task icon 216*e* may be a valuable tool for productivity, helping users keep track of their to-do lists.

In an embodiment, the interactive element 216 may include a find icon 216*f*, which may function as a search tool for locating specific information within the application. In an embodiment, the find icon 216*f* may allow users to quickly search through data, files, or content to pinpoint exactly what they need. In an embodiment, the find icon 216*f* may be especially useful in applications that manage large volumes of information or files. In an embodiment, the find icon 216*f* may enhance efficiency by reducing the time spent manually browsing through content. Continuing, by providing a fast search function, users may access information more quickly and effectively.

In an embodiment, the interactive element 216 may include an edit icon 216*g*, which may enable users to modify or update existing content within the application. Continuing, by clicking on the edit icon 216*g*, it may bring users to an editable version of the item, such as a text document, task, or file. In an embodiment, the edit icon 216*g* may allow users to make corrections or updates as needed, maintaining the accuracy of the information. In an embodiment, the edit icon 216*g* may ensure that content remains current and can be easily adjusted as situations or data change. In an embodiment, the edit icon 216*g* may be a crucial tool for users who frequently update or revise their work.

In an embodiment, the interactive element 216 may include a check box icon 216*h*, which may allow users to select or deselect items in a list or form. In an embodiment, the check box icon 216*h* may be used in task management systems to indicate whether a task has been completed or is still pending. In an embodiment, the check box icon 216*h* may allow a user to click the box to mark items as done or choose multiple options when interacting with a form. In an embodiment, the check box icon 216*h* may simplify user input by providing a clear, visual way to make selections. Check boxes may be intuitive tools for tracking progress or making choices.

In an embodiment, the interactive element 216 may include a scroll bar icon 216*i*, which may provide users with the ability to navigate through long pages of content. In an embodiment, the scroll bar icon 216*i* may be essential when the content exceeds the available screen space, allowing users to scroll vertically or horizontally. In an embodiment, the scroll bar icon 216*i* may help users move through information at their own pace, ensuring they can access all relevant content. In an embodiment, the scroll bar icon 216*i* may be particularly useful in applications with extensive data, such as documents or databases. In an embodiment, the scroll bar icon 216*i* may enhance the user interface by making navigation simple and intuitive.

In an embodiment, the interactive element 216 may include a text description 216*j*, which may provide additional information or context about a specific icon or feature. In an embodiment, the text description 216*j* may help users understand the purpose of an icon, making the interface more user-friendly. In an embodiment, the text description 216*j* may be displayed when a user hovers over an icon, providing clarification without cluttering the interface. In an embodiment, the text description 216*j* may improve the usability of the system, particularly for new or unfamiliar users.

Figure 2B:
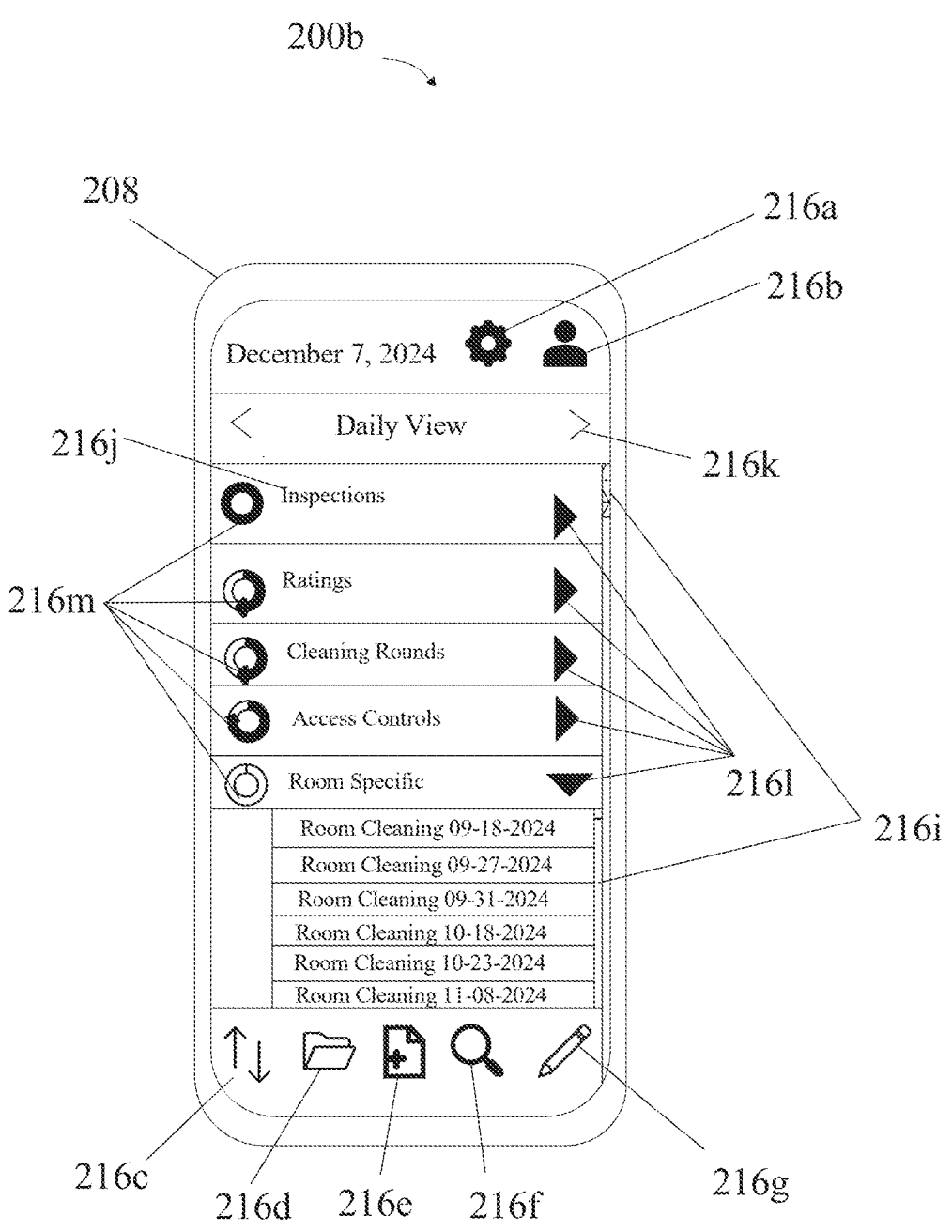
FIG. 2B is an exemplary illustration of a modified graphical user interface.

Referring now to FIG. 2B, an exemplary illustration 200*b* of a modified graphical user interface. In an embodiment, the interactive element 216 may include an arrow 216*k*. In an embodiment, the arrow 216*k* may serve as a directional indicator, guiding users to scroll, expand sections, or navigate between different pages or sections of the interface. In an embodiment, the arrow 216*k* may point in various directions, depending on its function, and may help improve the flow of user interaction by making navigation more intuitive. In an embodiment, the arrow 216*k* may be used in conjunction with other icons or features, signaling further actions the user may take. In an embodiment, the arrow 216*k* may enhance the overall user experience by making the interface more responsive and easier to use.

In an embodiment, the interactive element 216 may include a drop down carrot 216*l*. In an embodiment, the drop down carrot 216*l* may indicate the presence of a collapsible or expandable menu, allowing users to click on it to reveal additional options or settings. In an embodiment, the drop down carrot 216*l* may be placed beside menu items or sections where further choices or configurations are available. In an embodiment, the drop down carrot 216*l* may provide users with a way to hide or display extra content. In an embodiment, the drop down carrot 216*l* may contribute to a cleaner, more organized interface. Drop down carrot 216*l* may indicate historical data pertaining to the interactive element. In an embodiment, the drop down carrot 216*l* may assist in managing space on the screen, ensuring that users only see relevant information when needed.

In an embodiment, the interactive element 216 may include a progress circle 216*m*. In an embodiment, the progress circle 216*m* may be used to visually represent the progress of a task, such as a download, file upload, or completion of a process within the application. In an embodiment, the progress circle 216*m* may gradually fill or rotate as the task advances, providing users with real-time feedback on the status of their actions. In an embodiment, the progress circle 216*m* may help users gauge how much time remains for a task or process, reducing uncertainty and improving the overall usability of the system. In an embodiment, the progress circle 216*m* may be a helpful tool for keeping users informed and engaged.

Figure 2C:
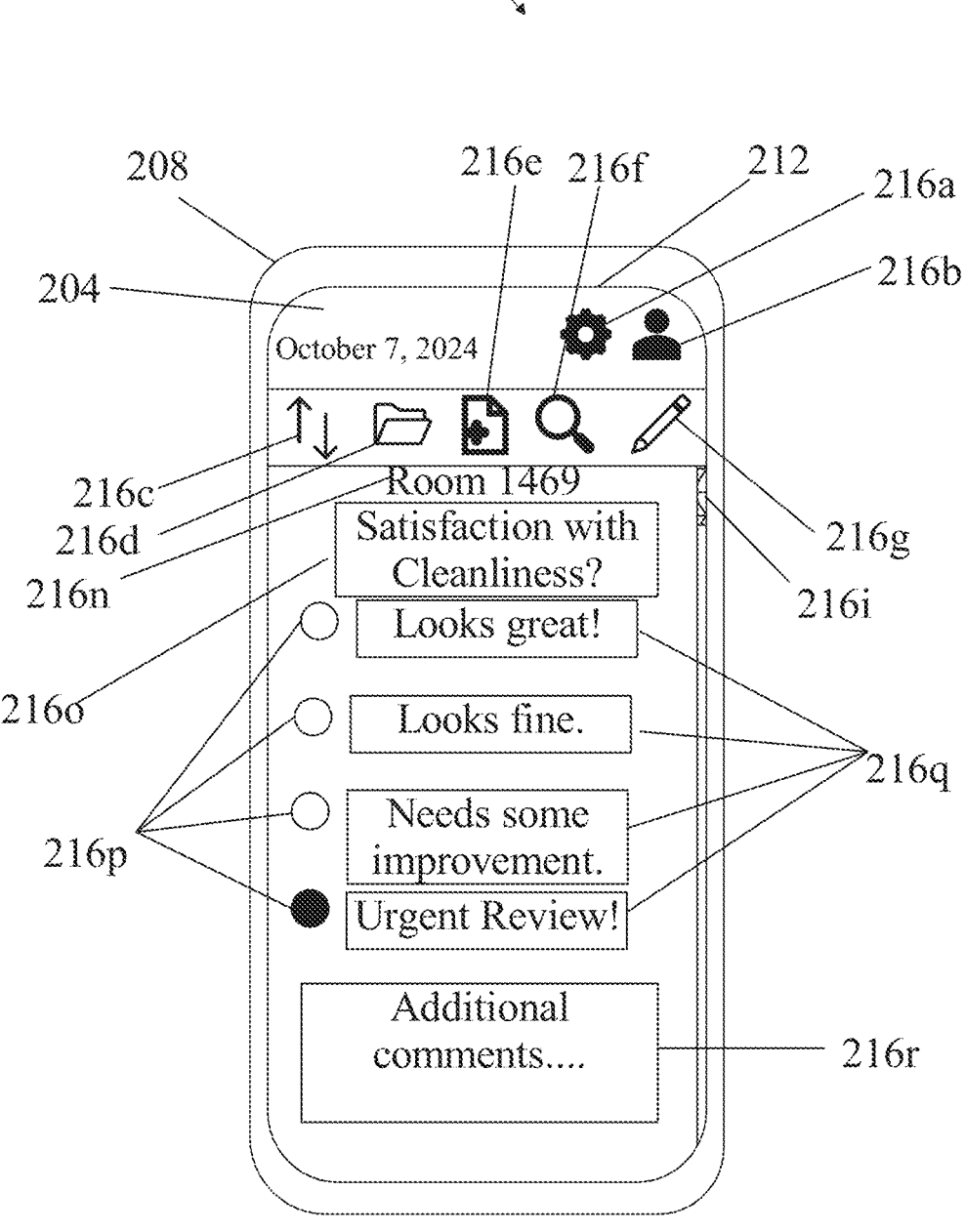
FIG. 2C is an exemplary illustration of a user interface at the first node.

Referring now to FIG. 2C, an exemplary illustration 200*c* of a user interface at the first node is illustrated. In an embodiment, the interactive element 216 may include an identifying indicator 216*n*. In an embodiment, 216*n* may represent an indicator of an identifying component, such as a room number or patient identifier, that provides context within the interface. In an embodiment, 216*n* may aid users in quickly identifying relevant data for specific patients or locations, streamlining navigation and enhancing contextual awareness within the system. In an embodiment, the interactive element 216 may include a textual icon 216*o*. In an embodiment, 216*o* may serve as a prompt for the rating interface element, guiding users to assess satisfaction or performance based on provided criteria. In an embodiment, the prompt may improve user engagement by clearly indicating where and how to provide ratings within the interface. The textual icon 2160 may thus make the rating feature more intuitive and accessible, prompting direct user interaction. In an embodiment, the interactive element 216 may include a multiple-choice icon 216*p*. In an embodiment, 216*p* represents a multiple-choice style for the rating interface element, allowing users to click on a rating datum to trigger the second execution operation. This multiple-choice format may simplify the rating process, enabling users to make selections quickly. In an embodiment, the multiple-choice icon 216*p* may contribute to an efficient user experience by reducing input complexity and facilitating clear, actionable feedback. In an embodiment, the interactive element 216 may include a text box 216*q*. In an embodiment, 216*q* may present phrasing indicating a satisfaction level that the first node can select. This feature may support a range of satisfaction ratings, encouraging users to choose an appropriate level based on their experience. In an embodiment, 216*q* may help capture detailed feedback by presenting clear options that align with specific satisfaction levels. In an embodiment, the interactive element 216 may also include a text entry box 216*r* for additional response data. In an embodiment, 216*r* may allow the first node to input additional response data surrounding their selected rating datum. This entry box may enable users to elaborate on their ratings, providing context or additional details. In an embodiment, the text entry box 216*r* may enhance the feedback process, allowing for more nuanced responses that can guide improvements or adjustments within the system.

Figure 2D:
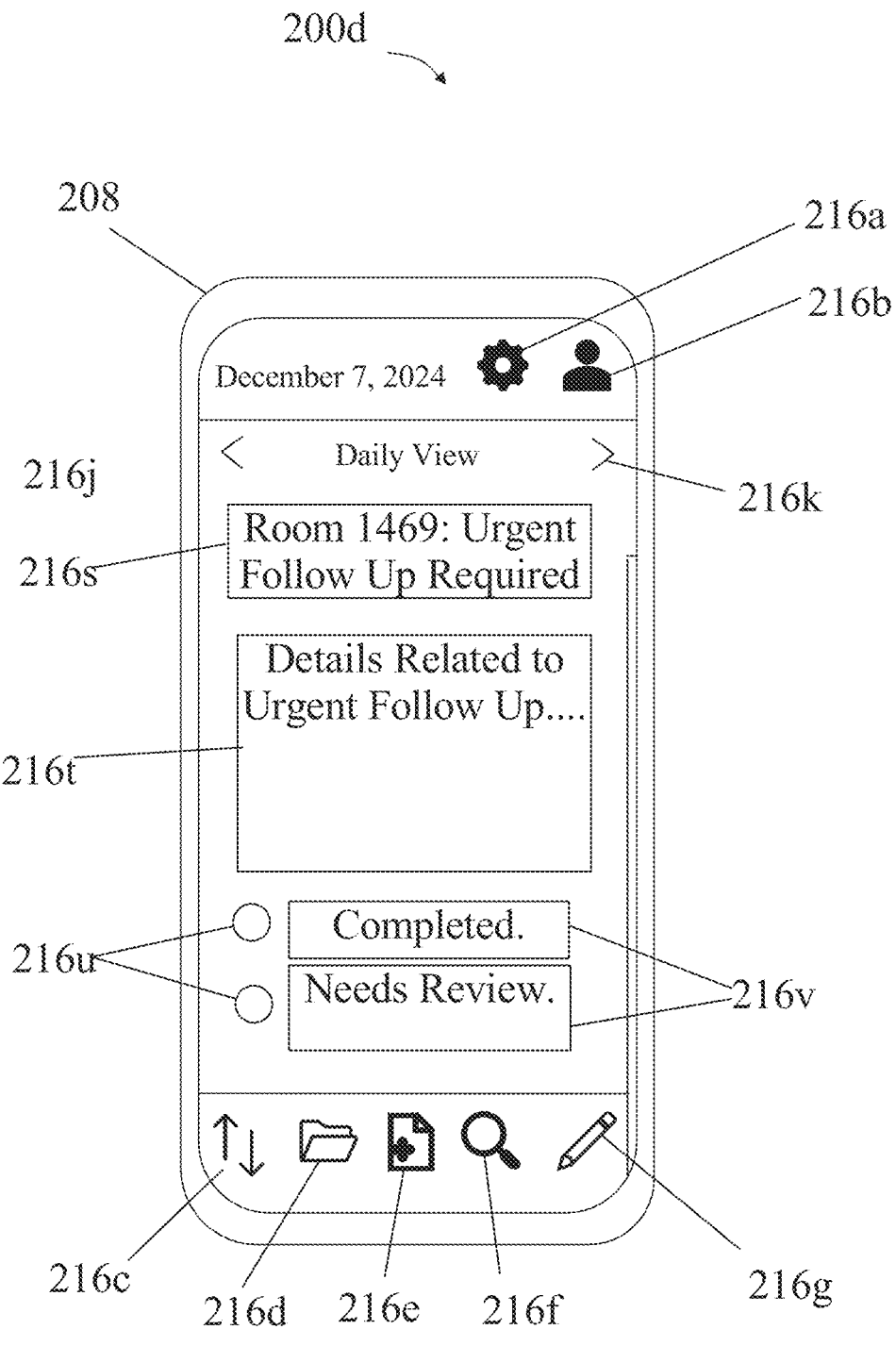
FIG. 2D is an exemplary illustration of a user interface at the assigned node.

Referring now to FIG. 2D, an exemplary illustration 200*d* of a user interface at the assigned node is illustrated. In an embodiment, the interactive element 216 may include a title indicator 216*s*. In an embodiment, 216*s* represents a title that displays identifying information and includes phrasing to indicate the priority level of the second execution operation. This title may provide the assigned user with essential context, helping them understand the urgency and specific nature of the task. In an embodiment, 216*s* may improve task clarity and prioritization by prominently displaying key information relevant to the operation. In an embodiment, the interactive element 216 may include a text box 216*t*. In an embodiment, 216*t* displays detailed information related to the second execution operation, which may be provided by the first node or drawn from other data sources. This text box may include specific instructions, background information, or relevant notes, offering comprehensive details to guide the user in executing the operation. In an embodiment, 216*t* enhances user understanding by presenting all necessary information within the interface, reducing the need for additional reference. In an embodiment, the interactive element 216 may include multiple-choice icons 216*u*. In an embodiment, 216*u* provides a selection of multiple-choice icons that the assigned node can choose from to indicate whether the second execution operation has been completed. This feature simplifies task tracking, allowing users to quickly log the completion status of the operation. In an embodiment, the multiple-choice icons 216*u* may contribute to a streamlined workflow, enabling easy status updates with minimal effort. In an embodiment, the interactive element 216 may also include text boxes 216*v* associated with the multiple-choice icons.

Figure 3:
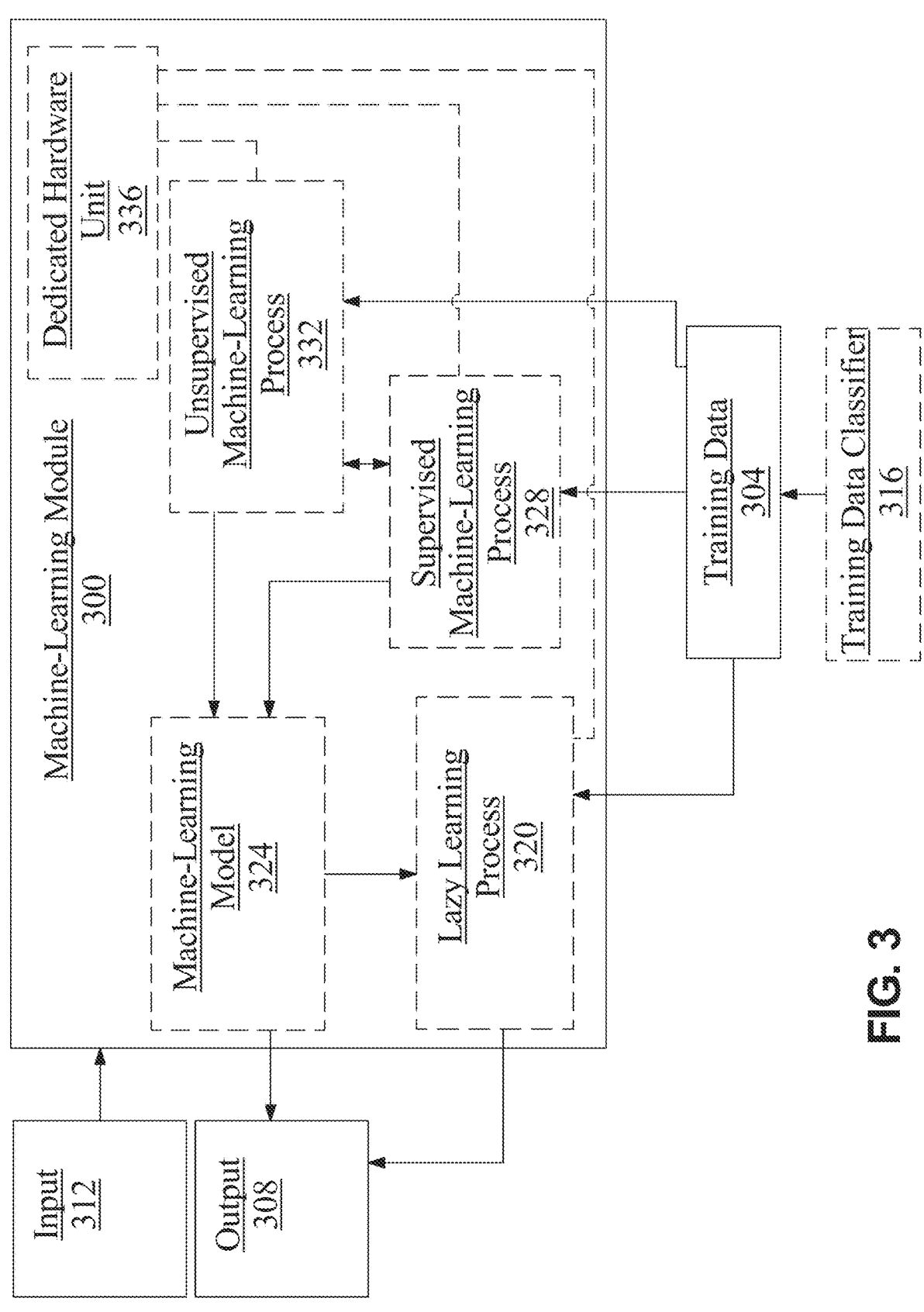
FIG. 3 is a block diagram of an exemplary machine-learning process.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example inputs such as user input and plurality of command input event handlers and outputs such as optimization datum.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to categories of historical reference data and categories of historical plurality of command input event handlers.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm May include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels.

It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25th percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include user input and plurality of command input event handlers as described above as inputs, optimization datum as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the clastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
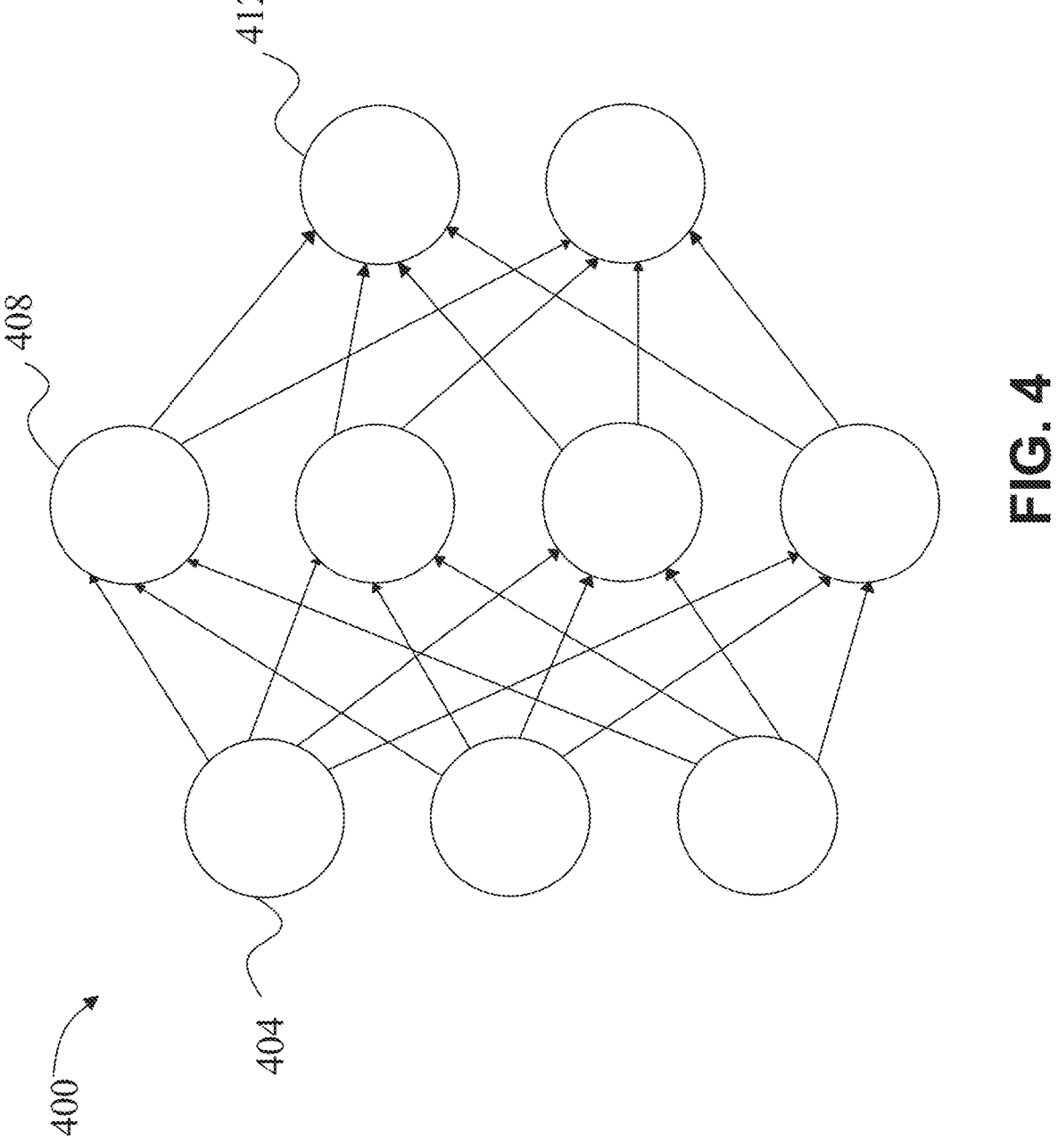
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
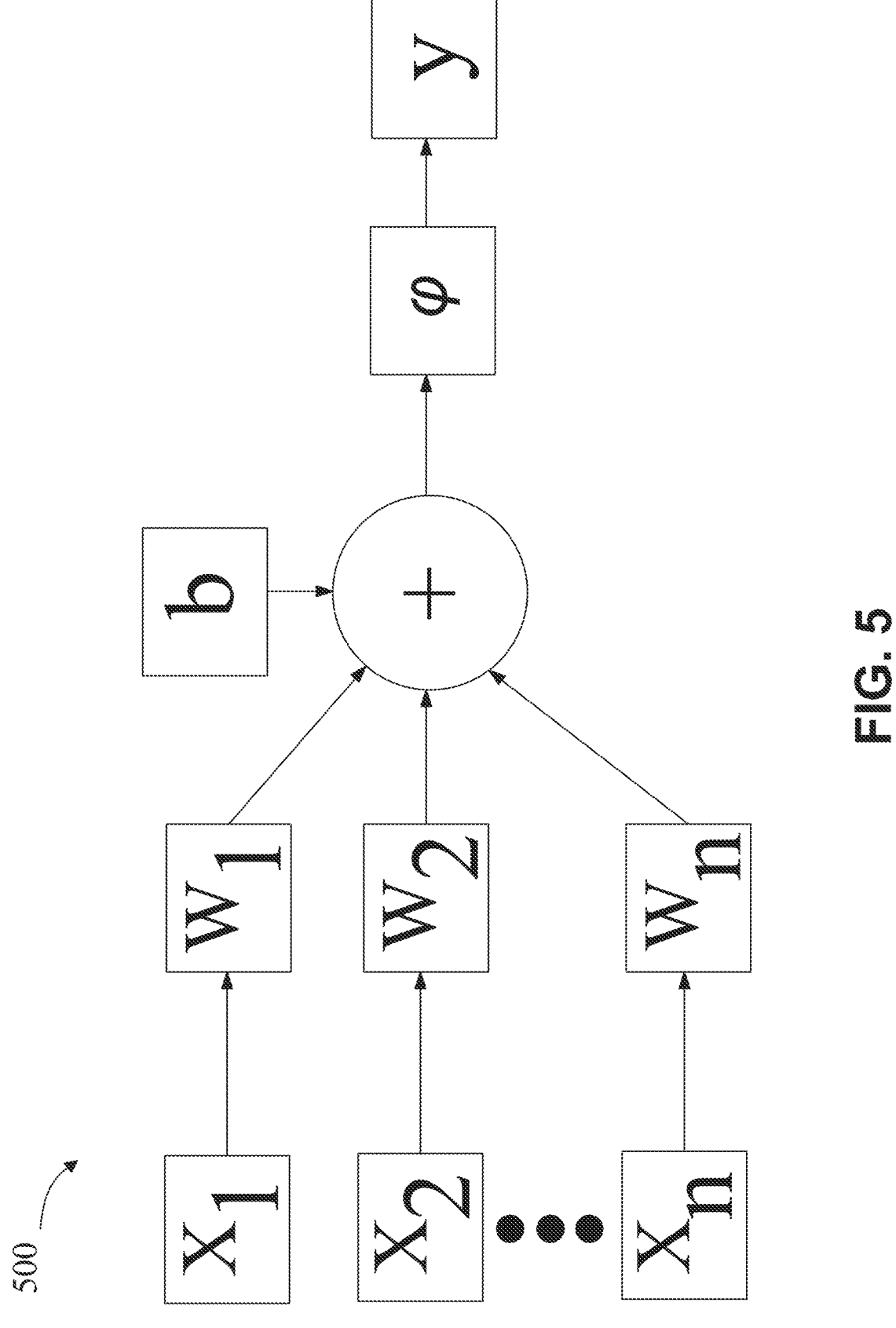
FIG. 5 is a diagram of an exemplary embodiment of a node of a neural network.

Referring now to FIG. 5, an exemplary embodiment of a node 500 of a neural network is illustrated. A node may include, without limitation, a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Referring now to FIG. 6, a flow diagram of an exemplary method 600 for generating a user-sensitive user interface is illustrated. At step 605, method 600 includes generating, by at least a processor, an execution operation as a function of a task module. This may be implemented as described and with reference to FIGS. 1-5.

Still referring to FIG. 6, at step 610, method 600 includes displaying, through the display device at a first node, the execution operations in a user interface. This may be implemented as described and with reference to FIGS. 1-5.

Still referring to FIG. 6, at step 615, method 600 includes receiving, through the user interface, user response data corresponding to one or more of the execution operations. This may be implemented as described and with reference to FIGS. 1-5.

Still referring to FIG. 6, at step 620, method 600 includes determining, by the at least a processor, as a function of the user response data, an assigned status corresponding to the one or more execution operations using a machine-learning model. This may be implemented as described and with reference to FIGS. 1-5.

Still referring to FIG. 6, at step 625, method 600 includes generating, by the at least a processor, a second execution operation and an assigned node as a function of the assigned status. This may be implemented as described and with reference to FIGS. 1-5.

Still referring to FIG. 6, at step 630, method 600 includes generating, by the at least a processor, an updated user interface as a function of the second execution operation and the assigned status. This may be implemented as described and with reference to FIGS. 1-5.

Still referring to FIG. 6, at step 635, method 600 includes transmitting, by the at least a processor, the updated user interface to the assigned node, wherein the assigned node is configured to display the updated user interface. This may be implemented as described and with reference to FIGS. 1-5. It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
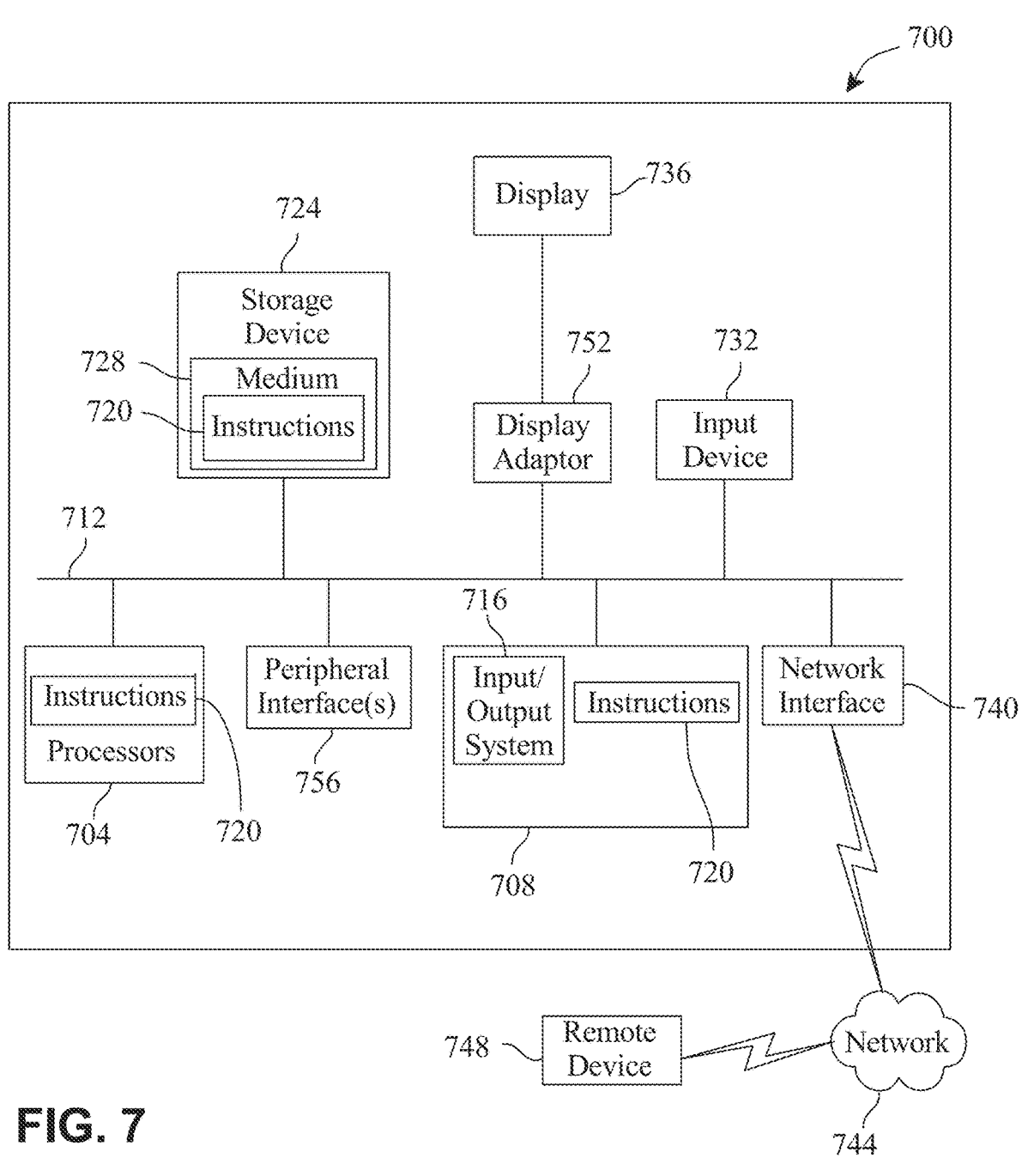
FIG. 7 is a block diagram of a computing system that can be used to implement any one or more of the methodologies disclosed herein and any one or more portions thereof.

FIG. 7 shows a diagrammatic representation of one embodiment of computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display 736. Examples of a display device include, but are not limited to, a liquid crystal display (LCD), a cathode ray tube (CRT), a plasma display, a light emitting diode (LED) display, and any combinations thereof.

Display adapter 752 and display 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a user-sensitive user interface, wherein the system comprises:
   at least a computing device, wherein the computing device comprises:
   a memory; and
   at least a processor communicatively connected to the memory, wherein the memory contains instructions configuring the at least a processor to:
   generate a graphical user interface comprising at least an interactive element associated with at least a visual element;
   receive user response data by the graphical user interface corresponding to one or more execution operations;
   determine, as a function of the user response data, an assigned status corresponding to the one or more execution operations using a machine-learning model;
   generate a second execution operation as a function of the assigned status;
   generate an updated user interface as a function of the second execution operation and the assigned status and comprises modifying the at least a visual element including a priority indicator to highlight new tasks generated from the second execution operation; and
   transmit the updated user interface to an assigned node, wherein the assigned node is configured to display the updated graphical user interface and further comprises:

identifying a current task load of each of a plurality of assigned nodes by querying the plurality of assigned nodes for information on their active tasks; and
   selecting an end user from at least one assigned node of the plurality of assigned nodes with a least number of pending tasks.

2. The system of claim 1, wherein receiving the user response data comprises receiving the user response data using a chatbot interface configured to receive a textual response style detailing an effectiveness of the one or more execution operations.

3. The system of claim 1, wherein determining the assigned status comprises:
   determining a tone of the user response data using a tonality classifier; and
   determining the assigned status as a function of the tone of the user response data.

4. The system of claim 1, wherein generating the second execution operation comprises generating the second execution operation as a function of a level of effectiveness of the assigned status.

5. The system of claim 1, wherein the updated user interface comprises contextual prompts related to the second execution operation.

6. The system of claim 1, wherein transmitting the updated user interface to the assigned node comprises:
   classifying the second execution operation to an end user pool; and
   selecting an end user from the end user pool wherein the end user is associated with the assigned node.

7. The system of claim 6, wherein transmitting the updated user interface to the assigned node comprises:
   generating a second assigned node as a function of the second execution operation being declined by the assigned node; and
   reclassifying to a second end user within the end user pool.

8. The system of claim 1, wherein transmitting the updated user interface comprises transmitting the updated user interface to the assigned node at specific intervals as a function of system requirements.

9. A method for generating a user-sensitive user interface, wherein the method comprises:
   generating, using at least a processor, a graphical user interface comprising at least an interactive element associated with at least a visual element;
   receiving, using the at least a processor, user response data by the graphical user interface corresponding to one or more execution operations;
   determining, using the at least a processor and as a function of the user response data, an assigned status corresponding to the one or more execution operations using a machine-learning model;
   generating, using the at least a processor, a second execution operation as a function of the assigned status;
   generating, using the at least a processor, an updated user interface as a function of the second execution operation and the assigned status and comprises modifying the at least a visual element including a priority indicator to highlight new tasks generated from the second execution operation; and
   transmitting, using the at least a processor, the updated user interface to an assigned node, wherein the assigned node is configured to display the updated graphical user interface and further comprises:

identifying a current task load of each of a plurality of assigned nodes by querying the plurality of assigned nodes for information on their active tasks; and selecting an end user from at least one assigned node of the plurality of assigned nodes with a least number of pending tasks.

10. The method of claim 9, wherein receiving the user response data comprises receiving the user response data using a chatbot interface configured to receive a textual response style detailing an effectiveness of the one or more execution operations.

11. The method of claim 9, wherein determining the assigned status comprises:

determining a tone of the user response data using a tonality classifier; and determining the assigned status as a function of the tone of the user response data.

12. The method of claim 9, wherein generating the second execution operation comprises generating the second execution operation as a function of a level of effectiveness of the assigned status.

13. The method of claim 9, wherein the updated user interface comprises contextual prompts related to the second execution operation.

14. The method of claim 9, wherein transmitting the updated user interface to the assigned node comprises:

classifying the second execution operation to an end user pool; and selecting an end user from the end user pool wherein the end user is associated with the assigned node.

15. The method of claim 14, wherein transmitting the updated user interface to the assigned node comprises:

generating a second assigned node as a function of the second execution operation being declined by the assigned node; and reclassifying to a second end user within the end user pool.

16. The method of claim 9, wherein transmitting the updated user interface comprises transmitting the updated user interface to the assigned node at specific intervals as a function of system requirements.

* * * * *